United States Patent
Rosenthal et al.

(10) Patent No.: US 6,612,976 B2
(45) Date of Patent: Sep. 2, 2003

(54) RADIOACTIVE MEDICAL DEVICES AND METHODS OF MAKING RADIOACTIVE MEDICAL DEVICES

(75) Inventors: David Rosenthal, Marietta, GA (US); Brian Gannon, Walpole, MA (US)

(73) Assignee: Isotech, L.L.C., Atlanta, GA (US)

( * ) Notice: Subject to any disclaimer, the term of this patent is extended or adjusted under 35 U.S.C. 154(b) by 0 days.

(21) Appl. No.: 09/879,551

(22) Filed: Jun. 12, 2001

(65) Prior Publication Data

US 2002/0058850 A1 May 16, 2002

Related U.S. Application Data

(63) Continuation-in-part of application No. 09/711,766, filed on Nov. 13, 2000.

(51) Int. Cl.$^7$ ............................ A61N 5/00; A61K 51/00
(52) U.S. Cl. ............................ 600/1; 424/1.65
(58) Field of Search ............... 600/1–8; 604/103.01; 514/449; 424/1.65, 9.36, 1.61

(56) References Cited

U.S. PATENT DOCUMENTS

| | | | | |
|---|---|---|---|---|
| 3,943,933 | A | | 3/1976 | Gertzman ................. 128/339 |
| 5,059,166 | A | | 10/1991 | Fischell et al. ............. 600/3 |
| 5,176,617 | A | | 1/1993 | Fischell et al. ............. 600/3 |
| 5,498,227 | A | * | 3/1996 | Mawad ...................... 600/3 |
| 5,709,644 | A | | 1/1998 | Bush ......................... 600/3 |

(List continued on next page.)

OTHER PUBLICATIONS

Intracoronary Irradiation Markedly Reduces Restenosis After Balloon Angioplasty in a Porcine Model, Journal of the American College of Cardiology, vol. 23, No. 6, pp. 1491–1498, May 1994; Joseph G. Wiedermann, MD, et al.

High Dose Rate Brachytherapy For Prevention Of Restenosis After Percutaneous Transluminal Coronary Angioplasty: Preliminary Dosimetric Tests Of A New Source Presentation, Int. J. Radiation Biol. Phys., vol. 33, No. 1, pp. 211–215, 1995; Youri Popowski, M.D., et al.

(List continued on next page.)

*Primary Examiner*—Eric F. Winakur
*Assistant Examiner*—Nikita R Veniaminov
(74) *Attorney, Agent, or Firm*—Thomas, Kayden, Horstemeyer & Risley, L.L.P.

(57) ABSTRACT

This invention involves radioactive medical devices for inhibiting an undesirable hyperplastic response in biological tissue, and a method for making the radioactive medical devices. In a first preferred embodiment, a medical device for inhibiting a hyperplastic response in biological tissue generally comprises polymeric hydrocarbon molecules forming the medical device and a salt or an acid of a radioactive isotope occluded within the polymeric hydrocarbon molecules. In a second preferred embodiment, the medical device comprises a thrombogenic sponge having a radioisotope trapped within the structure of the sponge. Also in a preferred embodiment, a method of creating a medical device according to the present invention comprises: providing a first solvent in a container; introducing a salt or an acid of a radioactive isotope into the first solvent; introducing a second solvent into the first solution so as to form a second solution; and introducing the medical device into the second solution, wherein the ionic components of the radioactive isotope migrate into the molecular structure of the medical device. In another aspect, a method of creating a medical device that inhibits a hyperplastic response in biological tissue comprises placing a salt or an acid of a radioactive isotope in a fluid and permitting the salt or acid to disassociate in solution, submersing the sponge in the solution and permitting the radioactive isotopes to become trapped in the structure of the sponge.

14 Claims, 4 Drawing Sheets

U.S. PATENT DOCUMENTS

| | | | |
|---|---|---|---|
| 5,795,286 | A | 8/1998 | Fischell et al. ................. 600/3 |
| 5,871,437 | A | 2/1999 | Alt ................................ 600/3 |
| 5,897,573 | A | 4/1999 | Rosenthal et al. ........... 606/224 |
| 5,942,209 | A | 8/1999 | Leavitt et al. .............. 424/1.25 |
| 5,977,163 | A * | 11/1999 | Li et al. ...................... 514/449 |
| 6,042,600 | A | 3/2000 | Rosenthal et al. ........... 606/224 |
| 6,106,454 | A | 8/2000 | Berg et al. ...................... 600/3 |
| 6,129,658 | A | 10/2000 | Delfino et al. ................. 600/3 |
| 6,306,073 | B1 * | 10/2001 | Weinberger ..................... 600/3 |
| 6,372,228 | B1 * | 4/2002 | Gregory ..................... 424/400 |
| 6,394,945 | B1 * | 5/2002 | Chan et al. ..................... 600/3 |
| 2001/0034363 | A1 * | 10/2001 | Li et al. ...................... 514/449 |

OTHER PUBLICATIONS

Endovascular Irradiation—A New Method To Avoid Recurrent Stenosis After Stent Implantation In Peripheral Arteries: Technique And Preliminary Results, Int. J. Radiation Oncology Biol. Phys, vol. 29, No. 1, pp. 183–186, 1994; H.D. Bottcher, M.D., et al.

Prophylactic Endovascular Radiotherapy to Prevent Intimal Hyperplasia after Stent Implantation in Femoropopliteal Arteries, CardioVascular and Interventional Radiology, vol. 17, pp. 12–16, 1994; Dieter Liermann, et al.

Catheter–Based Radiotherapy To Inhibit Restenosis After Coronary Stenting, The New England Journal of Medicine, vol. 336, No. 24, pp. 1697–1703, Jun. 12, 1997; Teirstein et al.

Intracoronary Low–Dose β–Irradiation Inhibits Neointima Formation After Coronary Artery Balloon Injury in the Swine Restenosis Model, Intracoronary β–Irradiation for Restenosis Circulation, vol. 92, No. 10, pp. 3025–3031, Nov. 15, 1995; Waksman et al.

Pure β–Particle–Emitting Stents Inhibit Neointima Formation in Rabbits, β–Particle–Emitting Stents Circulation, vol. 93, No. 4, pp. 641–645, Feb. 15, 1996; Hehrlein et al.

Effects of Endovascular Radiation From a β–Particle–Emitting Stent in a Porcine Coronary Restenosis Model, Dose–Response Effects of a β–Particle–Emitting Stent Circulation, vol. 94, No. 10, pp. 2364–2368, Nov. 15, 1996; Carter et al.

Inhibition of Neointimal Proliferation With Low–Dose Irradiation From a β–Particle–Emitting Stent, β–Particle–Emitting Stent Circulation, vol. 93, No. 3, pp. 529–536, Feb. 1, 1996; Laird et al.

Short– and Intermediate–Term Results of $^{32}$P Radioactive β–Emitting Stent Implantation in Patients With Coronary Artery Disease, $^{32}$P Radioactive Stent in Patients With CAD Circulation, pp. 18–26, Jan. 4/11, 2000; Albiero et al.

* cited by examiner

RADIOACTIVE MEDICAL DEVICES AND METHODS OF MAKING RADIOACTIVE MEDICAL DEVICES

CROSS-REFERENCE TO RELATED APPLICATION

This application is a continuation-in-part to copending U.S. patent application entitled, "Radioactive Medical Devices for Inhibiting a Hyperplastic Response and Method of Making Radioactive Medical Devices," having Ser. No. 09/711,766, filed Nov. 13, 2000, which is entirely incorporated herein by reference.

TECHNICAL FIELD

The present invention relates generally to medical devices and, more particularly, to a radioactive medical device having radiation emitting capabilities for inhibiting an undesired hyperplastic response to the healing of biological tissue, and a method for making and using the devices.

BACKGROUND OF THE INVENTION

In patients with vascular disease, cardiovascular surgeons use sutures to anastomose autogenous vein, prosthetic grafts, or arteries to other arteries in order to bypass around or replace diseased vessel segments. At virtually all anastomotic sites between the arteries, veins, and autogenous vein, or prosthetic grafts, a condition of rapid cellular growth termed "intimal hyperplasia" may occur.

Intimal hyperplasia is the usual response to blood vessel injury. This rapid cellular growth, as a response to injury of the blood vessel cellular lining, begins to narrow the opening between the vessels and/or graft to the point where an occlusion may occur. More specifically, intimal hyperplasia forms as a result of smooth muscle cell proliferation, migration, and extracellular matrix deposition. The interaction of platelets, macrophages, growth factors, and cytokines plays an important role in the process. Intimal hyperplasia is one of the primary cause of "restenosis" (narrowing) in the first year after vascular bypass operations. Usually, the patient must have another operation to revise or replace the occluded graft. If a major vein occludes (e.g. jugular or subclavian) massive edema of the upper extremity, face and neck may occur. If a limb artery occludes, it could possibly lead to potential limb loss.

Of course, intimal hyperplasia is merely a subset of a larger problem involving hyperplasia resulting from smooth muscle cell proliferation, migration, and extracellular matrix deposition. In general, when biological tissue begins grafting, or healing, an undesirable hyperplastic response may occur. It would be desirable to limit, or even prevent such an unwanted hyperplastic response.

One of the most frequently performed vascular surgical operation is an arterial to venous conduit for dialysis in chronic renal failure patients. Renal dialysis patients require repetitive angioaccess to this arterial-venous conduitive graft for dialysis to rid their system of the body's toxins. The most commonly used graft for dialysis in the United States is a prosethetic graft made from teflon or ePTFE (expanded polytetrafluroethylene). Unfortunately, as a consequence of repeated access by dialysis needles, these grafts fail frequently and have a primary occlusion rate of 15% to 50% during the first year, with a mean patency of only 15 months. One of the most common causes of failure in these grafts is due to the development of intimal hyperplasia at the venous anastomosis. Again, there is a strong desire in the art to prevent this unwanted hyperplastic response.

Both examples of tissue grafting stated above, operations necessary to treat arterial occlusive disease and an arterial to venous conduit for dialysis, prescribe the use of a suture to assist the healing of biological tissue. However, there are several devices currently used in the medical field for assisting the grafting of biological tissue. Amongst which may be, "patches," "wraps," and meshes which give the tissues time to heal. Similarly, stents come in a variety of configurations for supporting blood vessel walls in an attempt to inhibit stenosis of the vessel.

Surgical sutures are used to bring together ends of biological tissue and hold them in place until the joining tissues have time to heal. As another example, in some types of medical operations, medical personnel may use "patches" or meshes to support tissue in order to give the tissue appropriate time to heal. Just as with vascular bypass conduits, the tissue adjacent the "patch" or mesh may also exhibit signs of hyperplasia that are undesirable, if not harmful.

In recent years, studies have been conducted in animal models whose vessels have undergone balloon angioplasty. It was found that the vessels response to injury from balloon angioplasty is similar to that observed at suture anastomotic sites. Studies conducted at Emory University, Atlanta, Ga., U.S.A., and Vanderbilt University, Nashville, Tenn., U.S.A., suggest that restenosis results primarily from the migration and rapid proliferation of a smooth muscle type cell after balloon angioplasty. It has been demonstrated by these groups that very low levels of beta-particle irradiation introduced to the site of injury following angioplasty markedly inhibits smooth muscle cell proliferation and or migration. Numerous other studies have been conducted which have demonstrated and substantiated these early findings.

U.S. Pat. No. 5,897,573, filed Apr. 22, 1997, dealt with the problem of unwanted hyperplastic response in biological tissue by suggesting the irradiation of a suture material prior to its use in a patient. U.S. Pat. No. 5,897,573 describes how a low-level beta-emitting radioisotope may be incorporated into the chemical structure of suture material in order to inhibit an unwanted hyperplastic response. U.S. Pat. No. 5,897,573, filed Apr. 22, 1997, is hereby incorporated by reference as if fully set out herein.

Similarly, U.S. Pat. No. 6,042,600, filed Jan. 25, 1999, dealt with the problem of unwanted hyperplastic response in biological tissue by suggesting the irradiation of various medical devices before use in a patient. U.S. Pat. No. 6,042,600 was a continuation in part of U.S. Pat. No. 5,897,573. U.S. Pat. No. 6,042,600 describes how a low-level beta-emitting radioisotope may be incorporated into the chemical structure of a medical device. U.S. Pat. No. 6,042,600, filed Jan. 25, 1999, is hereby incorporated by reference as if fully set out herein.

Both of the two above-described patents generally prescribe chemically bonding the radioactive element to the structure of the medical device. However, there may be situations where it is not desirable to alter the chemical structure of the medical device to be used. Additionally, certain isotopes may not readily lend themselves to chemically attaching themselves to the molecules of the medical device. To remedy this need, U.S. Pat. Application having Ser. No. 09/711,766 was filed on Nov. 13, 2000. This patent application, also deals with radioactive medical devices. However, the devices are created by a process involving occluding salts of radioacitve isotopes into a molecular matrix of the medical device. U.S. Pat. Application having Ser. No. 09/711,766, filed Nov. 13, 2000, is hereby incorporated by reference as if fully set out herein.

SUMMARY OF THE INVENTION

Generally described, the present invention provides a radioactive medical device having radiation emitting capabilities for inhibiting an undesired hyperplastic response to the healing of biological tissue, and a method for making and using the devices. It is known that smooth muscle cell proliferation may be inhibited by varying degrees and types of radiation, particularly low level beta radiation and low level gamma radiation. This knowledge is exploited by the radioactive medical devices and method described herein.

In a first preferred embodiment, a method of creating a medical device that inhibits a hyperplastic response in biological tissue comprises the following steps: providing a first solvent in a container; introducing a salt or an acid of a radioactive isotope into the first solvent such that the salt or acid disassociates into ionic components so as to form a first solution; introducing a second solvent into the first solution so as to form a second solution; and introducing the medical device into the second solution, wherein the ionic components migrate from the second solution into the molecular structure of the medical device.

In another aspect, a method of creating a medical device that inhibits a hyperplastic response in biological tissue comprises the following steps: providing an organic solvent in a container; introducing a salt or an acid of a radioactive isotope into the organic solvent such that the salt or acid disassociates into ionic components so as to form a solution; and introducing the medical device into the solution, wherein the ionic components migrate from the solution into the molecular structure of the medical device.

In another aspect, a method of creating a medical device that inhibits a hyperplastic response in biological tissue comprises the following steps: providing an aqueous solution in a container; introducing a salt or an acid of a water soluble radioactive isotope into the aqueous solution such that the salt or acid disassociates into ionic components so as to form a second solution; and introducing the medical device into the second solution, wherein the ionic components migrate from the solution into the structure of the medical device.

In a first preferred embodiment of a medical device for inhibiting a hyperplastic response in biological tissue, the medical device generally comprises polymeric hydrocarbon molecules forming the medical device and a salt or an acid of a radioactive isotope occluded within the polymeric hydrocarbon molecules. As a result of this structure, the radioactive isotope in the polymeric hydrocarbon molecules of the medical device inhibits a hyperplastic response in biological tissue.

In another aspect of a medical device for inhibiting a hyperplastic response in biological tissue, the medical device comprises a thrombogenic sponge-like material having a radioactive isotope trapped within the structure of the sponge-like material. As a result of this structure, the radioactive isotope inhibits a hyperplastic response in biological tissue.

Other systems, methods, features, and advantages of the present invention will be or will become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

The present invention can be better understood with reference to the following drawings. The drawings are not necessarily to scale, emphasis instead being placed upon clearly illustrating the principles of the present invention. Moreover, like reference numerals designate corresponding parts throughout the several views.

DETAILED DESCRIPTION OF THE INVENTION

The present invention relates to conventional implantable medical devices that are designed to emit localized, low-level beta radiation while in or near biological tissue. The present invention also relates to both a method of preventing hyperplasia in biological tissue grafts and a method of creating medical devices that accomplish this goal.

Creation of the medical device of the present invention by a first preferred method begins with the selection of a radioactive isotope to be occluded into the molecular structure of the medical device. The preferred radioisotopes for the present invention are beta-emitting or gamma-emitting radioisotopes with relatively long half-lives. For purposes of this disclosure, a relatively long half-life is generally considered any half-life in excess of 150 days. However, it is possible to use radioisotopes with much shorter half-lives, as will be demonstrated below. Additionally, many of the radioisotopes that may be used have much longer half-lives than 150 days.

The preferred radioisotopes also emit a relatively low level of radiation. For purposes of this disclosure, a low level of beta radiation is generally in the range of 1000 uCi. Also for purposes of this disclosure, a low level of gamma radiation is similar to that of the beta range. Of course, one with skill in the art can readily determine the appropriate level of radiation to inhibit an undesired hyperplastic response. Such a level of radiation may not necessarily be within the above-specified range, and the present invention is not meant to exclude beta or gamma radiation values outside of this range. The range of radiation values is only illustrative and preferred for the particular embodiment described herein.

The following are examples of preferred beta-emitting radioisotopes: Calcium 45; Chlorine 36; Prometheum 147; Strontium 90; and Technitium 99. The following are examples of preferred gamma-emitting, and sometimes also beta-emitting, radioisotopes: Cobalt 60; Yttrium 90; Scandium 46; Cerium 141; Sodium 22; and Manganese 54. Most of the radioisotopes listed as examples have relatively long half-lives. Exceptions to this general property can be found with Scandium 46 (83 day half life) and Cerium 141 (32 day half life). This illustrates that radioisotopes with half lives of less than 150 days may also be preferred, depending on the particular application.

Although radioisotopes with short half-lives may also be effective with the present invention, a long half-life is preferred mainly due to storage and shipping concerns. Over time, the quantity of radioactivity of a radioisotope will decrease due to nuclear decay. The half-life is a measure of the rate of this decrease in radioactivity. If the quantity of radioactivity of the radioisotope decreases too rapidly, the medical device must be used almost immediately after manufacturing. This leaves no time for shipping and no flexibility as to storage of the medical device. For example, Prometheum 147, one of the above-listed radioisotopes, has a half-life of approximately 2.5 years. If Prometheum 147 is selected for the present invention, the 2.5 year half-life would provide ample time for manufacture, shipment, and storage. Then, when the medical device is needed, it still exhibits radioactive properties in adequate levels to provide the needed effect.

In the first preferred embodiment 10 of the present invention, Calcium 45 is selected. Calcium 45 is preferred for a variety of reasons. To begin, Calcium 45 has a half-life of about 163 days. This length of half-life is long enough to allow shipment and storage of the medical device. However, the fact that the half-life is not several years means that the medical device will not continue to be radioactive for many years after what is required to inhibit an undesirable hyperplastic response in a patient's biological tissue.

In the first preferred embodiment 10 of the method described below, the radioactive isotope, Calcium 45, is not used alone. Rather, a salt or an acid of the radioisotope is preferred. So, for example, the preferred isotope of Calcium 45 is used in the form of its salt, radioactive Calcium Chloride ($^{45}CaCl_2$). Of course, Calcium 45 could also be used in its acid form, however, in the preferred embodiment described below, radioactive Calcium Chloride is preferred. Even if the salt form of Calcium 45 is used, other salts are possible. For example, radioactive Calcium Fluoride ($^{45}CaF_2$) is a possible radioactive salt that can be used with the first preferred embodiment 10.

The other radioisotopes listed above can also be used in their salt or acidic form. For example, Chlorine 36 is used in the form of either radioactive Calcium Chloride ($Ca^{36}Cl_2$) or radioactive Hydrochloric Acid ($H^{36}Cl$); Prometheum 147 is used in the form of radioactive Prometheum Chloride ($^{147}PmCl_3$); Strontium 90 is used in the form of radioactive Strontium Chloride ($^{90}SrCl_2$) or radioactive Strontium Nitrate ($^{90}SrNo_3$); and Technitium 99 is used in the form of radioactive Technitium Fluoride ($^{99}TcFl_5$). As for the gamma-emitters listed above, for example, Cobalt 60 is used in the form of radioactive Cobalt Chloride ($^{60}PmCl_2$); Scandium 46 is used in the form of radioactive Scandium Chloride ($^{46}ScCl_3$); Cerium 141 is used in the form of radioactive Cerium Chloride ($^{141}CeCl_3$); Sodium 22 is used in the form of radioactive Sodium Chloride ($^{22}NaCl$); and Manganese 54 is used in the form of radioactive Manganese Chloride ($^{54}MnCl_2$).

The gamma-emitting radioisotope Yttrium 90 deserves special mention. If Strontium 90 is used in one of the forms listed above, as the Strontium breaks down, Yttrium 90 is the natural result. Thus, if Strontium 90 is selected, then the medical device will emit beta radiation for a time, and then will emit a low-level gamma radiation for the half-life of Yttrium 90. The radioactive Sodium Chloride mentioned above also has this characteristic. That is, radioactive Sodium Chloride initially emits beta radiation, and then over time, begins emitting gamma radiation as the Sodium 22 breaks down.

Figure 1:
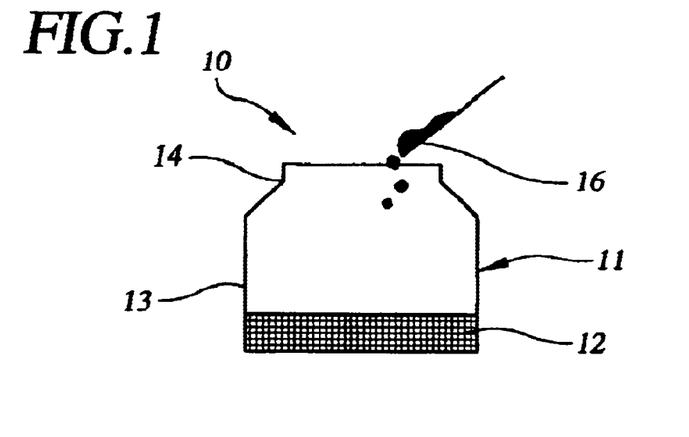
FIG. 1 is a cut-away side view of the first step used in the method of the first preferred embodiment.
Figure 2:
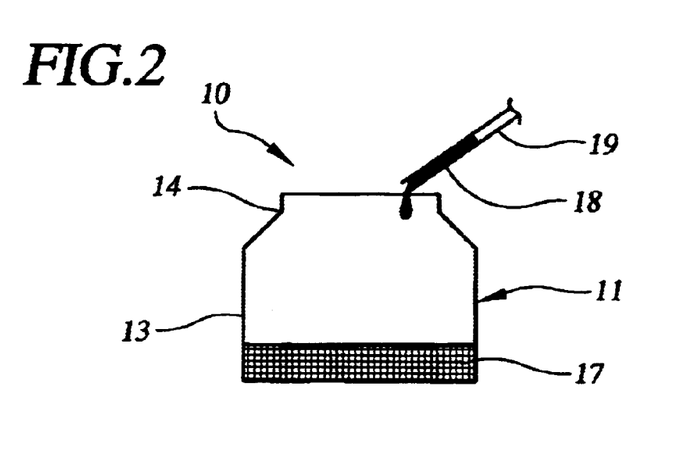
FIG. 2 is a cut-away side view of the second step used in the method of the first preferred embodiment.
Figure 3:
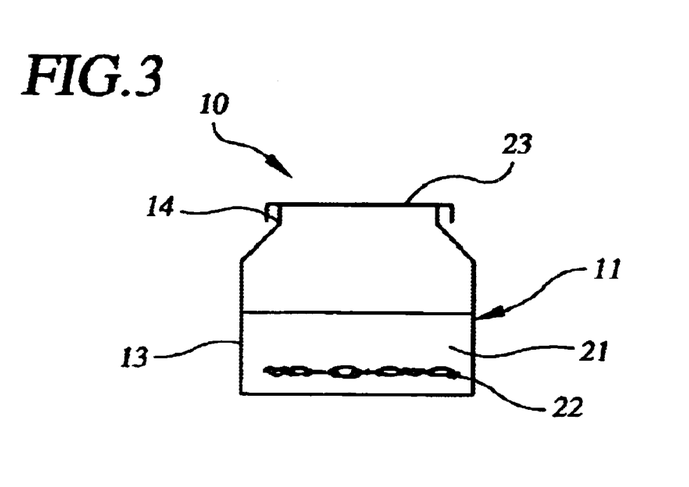
FIG. 3 is a cut-away side view of the third step used in the method of the first preferred embodiment.

FIGS. 1–3 depict a first preferred embodiment 10 of a method for creating a radioactive medical device according to the present invention. In FIG. 1, a container 11 is depicted with a solvent 12 in the container 11. The container has a body portion 13 and a neck portion 14. Initially, the solvent 12 is placed in the body 13 of the container 11.

The solvent 12 of the first preferred embodiment 10 is a protic solvent. More specifically, the preferred protic solvent for the present invention is Ethyl Alcohol ($C_2H_5OH$). Of course, other protic solvents may be used, such as ethyl acetate ($CH_3COOC_2H_5$) or toluene ($C_6H_5CH_3$). In the specific preferred embodiment described herein, the amount of Ethyl Alcohol is 0.5 milliliters. The amount of solvent 12 will generally vary with the size of the medical device to be immersed in the radioactive solution and other practical considerations. One skilled in the art will be able to determine the appropriate amount of solvent 12 to be used for a specific application.

Although glass is the preferred material of the container 11, other types of containers may be used. Generally, it is desirable to use a container 11 that is relatively non-reactive. Also, the shape of container 11 depicted in FIG. 1 is also not important to the present invention. Any shape will suffice, as long as the opening of the container 11, as defined by the neck 14, is sufficiently large to accept a medical device to be exposed to a radioactive solution in the container 11. As will be outlined below, the container 11 of the preferred embodiment is also able to accept a lid, or to be sealed in some other way.

The preferred form of a radioisotope 16 is added to the Ethyl Alcohol 12. See FIG. 1. As noted above, the preferred radioisotope is a salt of the beta-emitting Calcium 45, radioactive Calcium Chloride ($^{45}CaCl_2$). Other salts or acids could be used. Also, a gamma-emitting radioisotope could also be used. In the preferred embodiment, 60 millicuries of radioactive Calcium Chloride 16 is added into the container 11 and allowed to dissolve in the Ethyl Alcohol 12. In this way, the Ethyl Alcohol 12 serves to reduce the radioactive Calcium Chloride 16 into solution. When introduced into the Ethyl Alcohol 12, the radioactive Calcium Chloride 16 dissociates into its component ions: $^{45}Ca^{(+)}$ and $Cl^{(-)}$. The radioactive Calcium Chloride 16 will remain dissociated into solution without any solid crystals in the container 11. Physically, the Ethyl Alcohol 12 forms a type of matrix around the $^{45}Ca^{(+)}$ and $Cl^{(-)}$ ions in order to keep the ions dissociated in solution form.

The solution 17 formed by the radioactive Calcium Chloride 16 and the Ethyl Alcohol 12 is depicted in the container 11 in FIG. 2. Once the radioactive Calcium Chloride 16 is dissolved into the Ethyl Alcohol 12, a second solvent 18 is added to the container 11, as depicted in FIG. 2. This second solvent 18 is preferably capable of expanding the molecular matrix of a polymer structure. To this end, the preferred second solvent 18 is Methylene Chloride ($CH_2Cl_2$). However, dimethylformamide and tetrahydrofuran would also function adequately, although they typically do not function as well as Methylene Chloride.

In the first preferred embodiment 10, 19 milliliters of Methylene Chloride 18 is added to the container 11 in batches of less than 5 milliliters at a time. In the first preferred embodiment 10, a glass pipette 19 is used to hold and then dispense the 19 milliliters in four separate batches. In this way, the Methylene Chloride 18 is slowly added to the solution 17 in the container 11. The Methylene Chloride 18 is added slowly to the solution 17 in order to prevent causing the $^{45}Ca^{(+)}$ and $Cl^{(-)}$ ions to leave solution and form crystals of radioactive Calcium Chloride along the bottom of the container 11.

The combination of Methylene Chloride 18 and the Ethyl Alcohol/Calcium Chloride solution 17 form a new solution 21. Because Methylene Chloride 18 and Ethyl Alcohol 12 are miscible fluids, the new solution 21 will be a blend of Methylene Chloride 18 and Ethyl Alcohol 12. Because the $^{45}Ca^{(+)}$ and $Cl^{(-)}$ ions are in ionic suspension within the Ethyl Alcohol 12, the new solution 21 will generally comprise an homogenous distribution of $^{45}Ca^{(+)}$ and $Cl^{(-)}$ ions.

Once all the Methylene Chloride 18 has been added to the container 11, a medical device 22 to be exposed to the radioactive solution 21 is placed in the container 11. In the first preferred embodiment 10, the medical device 22 is a mesh material, as shown more clearly in FIG. 4. The mesh material 22 is preferably constructed of polypropylene. In use, a medical practitioner may wrap this polypropylene mesh 22, once it is labeled with a beta emitting radioactive substance, around a graft site in order to bathe the site with beta radiation. The use of this particular medical device 22 will be described in greater detail below.

Of course, many different types of medical devices may benefit from having the capacity to emit low level localized beta or gamma radiation, and the present invention is not intended to be limited to a polypropylene mesh. Generally, any place that a medical device may be used in a body, the advantages afforded by the capability of emitting beta or gamma radiation may be helpful. For example, and without limitation, the medical devices of the present invention may comprise: surgical sutures, stents, surgical patches, anti-thrombogenic coatings, hydrophilic coatings, coverings or weavings over stents, fabric or mesh implants in the body, coatings on or woven into plastic catheters (e.g. dialysis catheters), biodegradable materials, thrombogenic sponges and gelfoams, and ocular lens implants.

Figure 4:
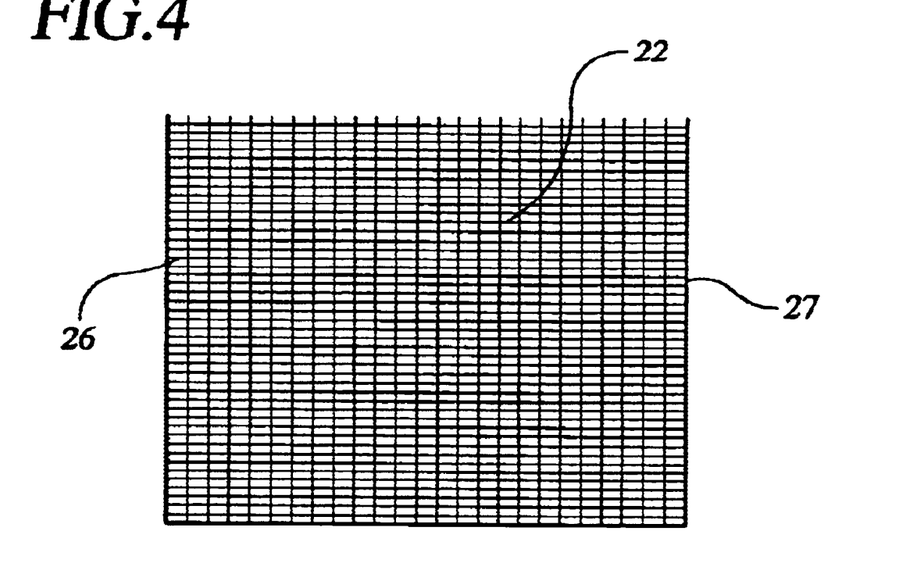
FIG. 4 is a plan view of a mesh material of the first preferred embodiment.

As noted above, in the first preferred embodiment 10, the mesh 22 is constructed of a polypropylene material. Polypropylene is a biocompatable material. However, in an alternative embodiment, the mesh material could be another biocompatable hydrocarbon material, such as polyethylene. In another alternative embodiment, the mesh material could comprise a biodegradable material.

As depicted in FIG. 3, the mesh 22 is placed in the solution 21. The mesh 22 is preferably completely submerged within the solution 21. Once the mesh 22 is placed in the container 11, a covering 23, or lid, is placed on the neck 14 of the container 11 in order to seal the container 11. If no lid 23 is used, the solution 21 will likely begin to evaporate. This may be undesirable if the mesh 22 is to stay in the solution 21 for several days.

Once the mesh 22 is in the solution 21, the Methylene Chloride 18 in the solution 21 expands the polypropylene matrix 24 and the $^{45}Ca^{(+)}$ and $Cl^{(-)}$ ions begin migrating into and among the molecular structure 24 of the polypropylene mesh 22. The mesh 22 is left in solution 21 until the desired concentration of radioactive Calcium is reached. In other words, the mesh 22 is left in solution 21 until it has incorporated the desired level of radiation-emitting characteristics. The migration of the radioactive Calcium may take anywhere from a day, to several days, to several weeks. The length of time necessary for migration of the radioactive ions into the molecular structure of the mesh 22 depends on the concentration of the radioactive ion present in the solution. In the preferred example, a one inch square of polypropylene mesh 22 is preferably left in the container 11 for 6–8 weeks.

One skilled in the art can readily determine the appropriate length of time to expose the mesh 22 to the radioactive Calcium in the solution 21. For example, small portions of the mesh 22 can be cut and tested to determine the level of radiation emitted by the irradiated mesh 22. If the level is too low, then the mesh 22 is left in solution 21. On the other hand, if the level of radioactive Calcium in the mesh 22 has reached equilibrium, or the desired level of radioactivity, then the mesh 22 is removed from the solution 21.

Figure 5:
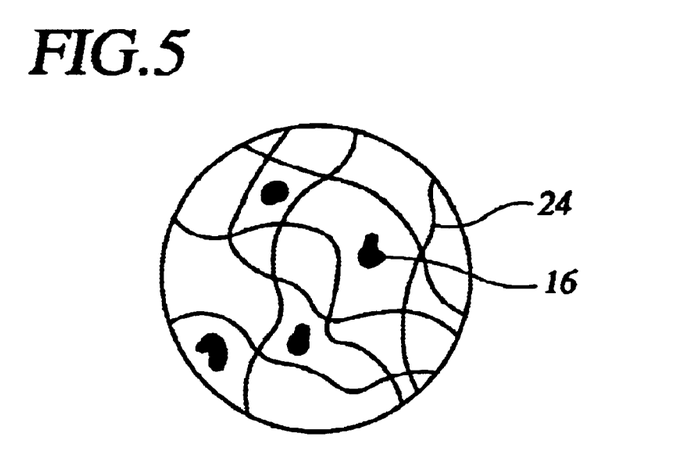
FIG. 5 is an exploded top depiction of the fibers of the mesh material depicted in FIG. 4.

After reaching the desired concentration of radioactive material in the mesh 22, the mesh 22 is removed from the container and permitted to dry. As the mesh 22 dries, the $^{45}Ca^{(+)}$ and $Cl^{(-)}$ ions re-form radioactive Calcium Chloride ($^{45}CaCl_2$) crystals 16, while still in the plastic mesh 22. It should be recalled that the Methylene Chloride caused the plastic fibers 24 to swell when the mesh 22 was placed in the solution 21. At the same time the $^{45}Ca^{(+)}$ and $Cl^{(-)}$ ions are reforming radioactive Calcium Chloride 16, the drying process causes the polypropylene matrix 24 of the mesh 22 to shrink back to its original shape. This shrinkage causes the radioactive Calcium Chloride crystals 16 to become occluded in the polypropylene molecules 24. FIG. 5 depicts an exploded view of one strand of the mesh 22 in order to demonstrate the occlusion of the radioactive Calcium Chloride 16 in the polypropylene fibers 24 of the mesh 22. Thus, radioactive Calcium Chloride crystals 16 are dispersed throughout the plastic polymer structure and held in place by the polypropylene matrix 24.

In the first preferred method 10, after drying is complete, the mesh 22 is rinsed several times with Ethyl Alcohol 16. Rinsing the mesh 22 removes any remaining Methylene Chloride 18 from the fibers and also removes any radioactive Calcium Chloride molecules that are not trapped within the molecular structure 24 of the mesh 22. Rinsing the mesh 22 with Ethyl Alcohol 16 also serves to clean and sterilize the mesh material.

Ethyl Alcohol is not the only liquid that may be used to rinse the mesh material. If rinsing is desired, the mesh may be rinsed with a variety of other solutions which are equally effective at removing Methylene Chloride and free radioactive ions. Of course, rinsing the mesh material is not required by the present invention.

Generally, a solvent like Methylene Chloride will re-expand the polypropylene fibers 24 of the mesh 22, thereby releasing the radioactive Calcium Chloride crystals 16. Water and bodily fluids are typically not of this nature and will not re-expand the molecular chain structure 24 of the polypropylene mesh 22 sufficiently to release the radioactive Calcium Chloride crystals 16. So, the radioactive calcium chloride molecules 16 stay trapped in the molecular structure 24 of the mesh 22 and will not migrate out of the mesh 22 when the mesh 22 is either handled or implanted into a patient's body.

The mesh 22 of the first preferred embodiment 10 is typically used in surgical procedures in order to inhibit hyperplasia resulting from smooth muscle cell proliferation, migration, and extracellular matrix deposition. As noted above, when biological tissue begins healing, an undesirable hyperplastic response may occur, such as intimal hyperplasia. The mesh material 22 of the preferred embodiment may be used to inhibit this undesirable hyperplastic response.

In order to use the mesh 22 to inhibit an unwanted hyperplastic response, a surgeon typically wraps the mesh 22 of the preferred embodiment around a site where tissues have been grafted, such as by a suture. Once the mesh 22 is placed around the graft site, the surgeon simply stitches the ends 26, 27 of the mesh 22 together in order to secure it in place. Of course, anywhere biological tissues are grafted together, the mesh 22 of the preferred embodiment will be very beneficial in preventing undesirable hyperplasia. For example, the mesh 22 could be placed between the tissues to be grafted. In this way, the device holding the tissue together, such as a suture, would also secure the mesh 22 into place. One with skill in the art will be able to see many additional uses for the medical device 22 of the first preferred embodiment 10.

The method of incorporating radioactive material into a medical device described with regard to a polypropylene mesh 22 above could be used similarly to radioactively label a whole host of medical devices. Such devices may include (without limitation): surgical sutures, stents, surgical patches, anti-thrombogenic coatings, hydrophilic coatings, a covering or weaving over stents, fabric or mesh implants in the body, coatings on or woven into plastic catheters (e.g. dialysis catheters), biodegradable materials, thrombogenic sponges or gelfoams, and ocular lens implants. If one of these other medical devices are radioactively labeled by the above-described method, then these devices will also inhibit undesirable hyperplasia.

If certain medical devices are used with the present invention, such as suture material for example, then it may be desirable to incorporate the preferred salt of a radioactive isotope into a polymeric hydrocarbon material before the medical device is actually made, or while the device is being made. For example, Calcium 45, or other beta or gamma emitting isotope could be introduced into the polymeric hydrocarbon material during a blending or extruding process used to make the medical device.

Also, certain medical devices may permit the use of alternative methods of making the medical device radioactive. For example, it is common in various types of surgical procedures to use a sponge-like material to assist in achieving hemostasis at a graft site. Such sponges are typically constructed of a synthetic cellulose material, although the present invention is not limited to sponges constructed from this particular material. One such hemostatic agent is a thrombogenic sponge product known as Gelfoam®, manufactured by the Pharmacia Corporation.

These thrombogenic sponge-like materials, like Gelfoam®, typically are manufactured into substantially planar sheets resembling a Styrofoam-like material. The sponge material may be treated with prothrombin, although not required by the present invention. Prothrombin is basically a carbohydrate-protein compound that is naturally occurring in blood plasma. Prothromin is essential to blood clotting. For use, medical practitioners cut the material to the size of sponge needed. When ready for use, the medical practitioner places the "patch" of sponge material in an aqueous solution, usually isotonic saline. Sponge-like materials, such as Gelfoam®, are typically water soluble, though not immediately soluble. Therefore, the sponge begins to soften in the aqueous solution, although this takes some time.

If the sponge is treated with prothrombin, the aqueous solution also serves to convert the prothrombin into thrombin. When used in the body, this thrombin will convert fibrinogen into fibrin at the graft site, which along with the patient's platelet cells, will assist in clotting.

Once the sponge-like material becomes pliable, the medical practitioner may better use the sponge. The medical professional removes the sponge from the solution and places it on the site to be treated. Materials of this type are used at suture-line sites to assist in the establishment of hemostasis. One of the advantages of using the sponge is that the sponge circumferentially covers the site so that the site is fully bathed with the thrombin, or other material delivered to the site by the sponge.

It would be beneficial in many application if the sponge material were treated so that it emitted radiation in order to inhibit a hyperplastic response. Thus, the sponge could be used to both assist in the clotting function and then inhibit hyperplasia. Because sponges like Gelfoam® are typically not constructed of hydrocarbon molecules, the first preferred embodiment for incorporating a radioisotope into a medical device described above may not be entirely successful in incorporating radioisotopes into the structure of the sponge. The Methylene Chloride of the above-described method will not cause the molecular structure of the sponge to swell appreciably in the same manner as it causes plastic molecules to swell. Also, because the sponge is water soluble, the protic solvent of the first preferred embodiment will begin to dissolve the sponge. This is not desirable until immediately before the sponge is to be used by the medical practitioner.

Figure 6:
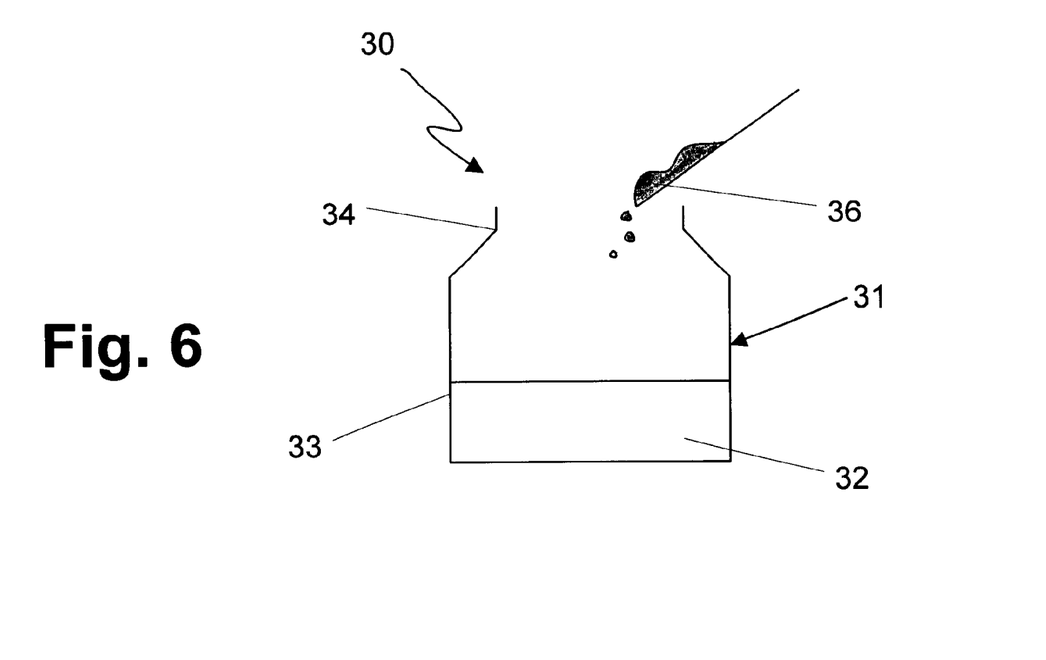
FIG. 6 is a cut-away side view of the first step used in the method of the second preferred embodiment.
Figure 7:
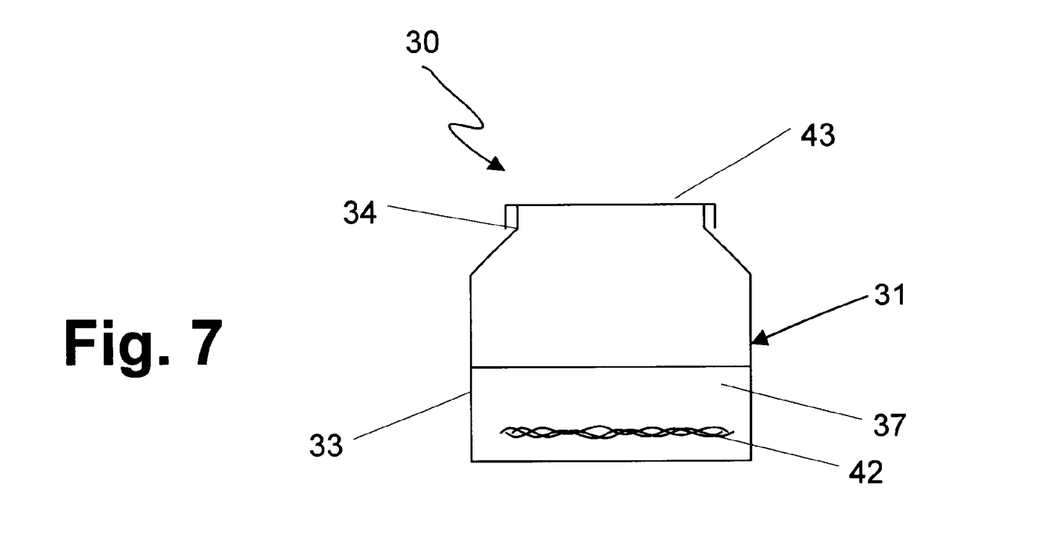
FIG. 7 is a cut-away side view of the second step used in the method of the second preferred embodiment.

For these reasons, in a second preferred embodiment of a method for making a radioactive medial device a surgical sponge material, such as Gelfoam®, is caused to incorporate a radioisotope for delivery to an injury site in a patient. FIGS. 6–7 depict the second preferred embodiment 30 of a method for creating a radioactive medical device according to the present invention. In FIG. 6, a container 31 is depicted. The container has a body portion 33 and a neck portion 34. Although glass is the preferred material of the container 31, other types of containers may be used. Generally, it is desirable to use a container 31 that is relatively non-reactive. Also, the shape of container 31 depicted in FIG. 6 is not important to the present invention. Any shape will suffice, as long as the opening of the container 31, as defined by the neck 34, is sufficiently large to accept the sponge material to be exposed to a radioactive solution in the container 31. The container 31 of the preferred embodiment is also able to accept a lid, or to be sealed in some other way. However, an alternative container would comprise a simply glass dish.

As depicted in FIG. 6, an organic solvent 32 is placed in the container 31. The preferred organic solvent 32 is ethanol. However, many other organic solvents would function with the preferred embodiment, as would be understood by one having ordinary skill in the art. Once the organic solvent 32 is in the container 31, a radioactive nonwater soluble salt 36 is added to the organic solvent 32. The radioactive non-water soluble salt 36 of the second preferred embodiment 30 is radioactive Calcium Carbonate ($^{45}CaCO_3$). The preferred radioactive Calcium Carbonate uses Calcium 45, which has all the advantages outlined above with respect to the first preferred embodiment 10. Of course, other non-water soluble salts could also be used with the second preferred embodiment 30 if a different radioisotope is preferred. For example, if Strontium 90 is the preferred radioisotope, $^{90}Sr(PO_4)_2$ is an appropriate non-water soluble salt of Strontium 90.

The radioactive Calcium Carbonate 36 will disassociate in the organic solvent 32 into $^{45}Ca^{(++)}$ and $CO_3^{(--)}$ ions. The organic solvent 32 and the ionic components of radioactive Calcium Carbonate will form a solution 37 in the container. The Calcium Carbonate typically fully dissolves in about 24 hours. One with ordinary skill in the art will readily be able to determine the time needed to permit radioactive Calcium Carbonate 36 to dissociate in the organic solvent 32.

Once the radioactive Calcium Carbonate 36 dissociates into solution 37, a sponge 42 to be treated is placed in the solution, as shown in FIG. 7. Because the sponge 42 in the preferred embodiment 30 is water soluble, the sponge 42 will not begin to break down in the organic solvent solution 37. However, the $^{45}Ca^{(++)}$ and $CO_3^{(--)}$ ions will begin to migrate into the structure of the sponge 42. It is preferred that that sponge material absorb adequate $^{45}Ca^{(++)}$ ions to give the sponge a level of radioactivity need to inhibit a hyperplastic response in biological tissue. This level of radioactivity could be, for example, about 250 uCi per square inch of sponge 42. To achieve this level of radioactivity, the solution 37 is preferably proportioned with radioactive Calcium Carbonate and organic solvent so that it exhibits radioactivity of about 10 mCi/ml. Once the sponge 42 is submerged in the solution 37, a lid 43 is added to cover the neck region 34 of the container 31. The sponge material 42 is preferably left in the solution 37 up to about 7 days, although the present invention is not so-limited. The time the sponge 42 is left in the solution 37 depends on the properties, size and thickness of the sponge 42.

Once the desired level of radioactivity is reached, the sponge material 42 is removed from the solution 37 and allowed to dry. As the sponge 42 dries, the $^{45}Ca^{++}$ and $CO_3^{--}$ ions will reassociate into radioactive Calcium Carbonate. However, the radioactive Calcium Carbonate will be trapped within the natural fibers and recesses of the sponge material 42. Once dry, the sponge 42 may then be packaged and shipped to a medical professional for use.

As noted above, when ready to use the sponge material, the medical professional typically places the sponge in an aqueous solution. As radioactive Calcium Carbonate is not water soluble, the ions will not dissociate in the aqueous solution. Thus, when the sponge is removed from the aqueous solution and placed in or on biological tissue, the radioactivity of the sponge is preserved. That is, radioactivity is typically not left in the aqueous solution.

Figure 8:
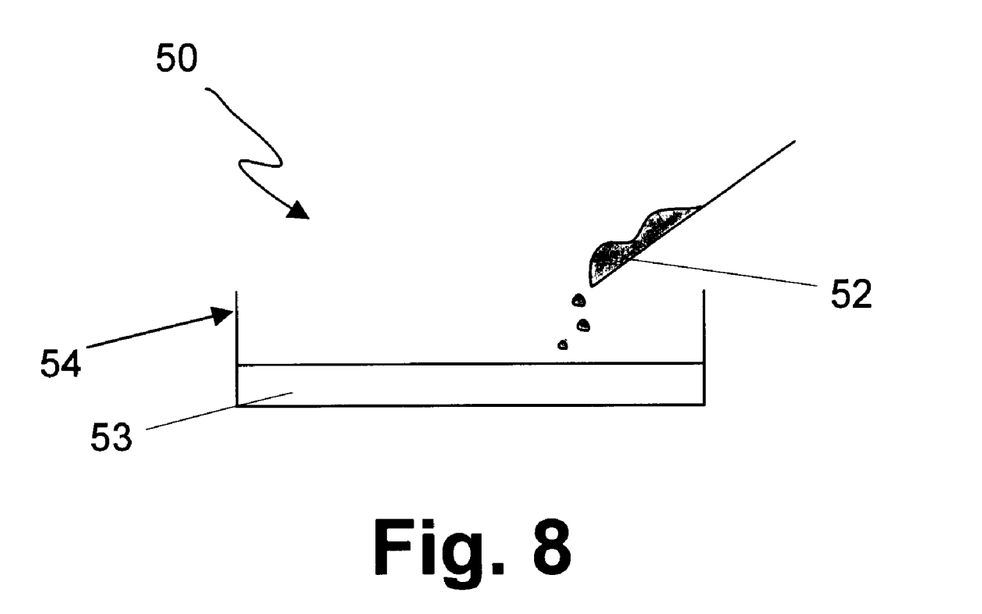
FIG. 8 is a cut-away side view of the first step used in the method of the third preferred embodiment.
Figure 9:
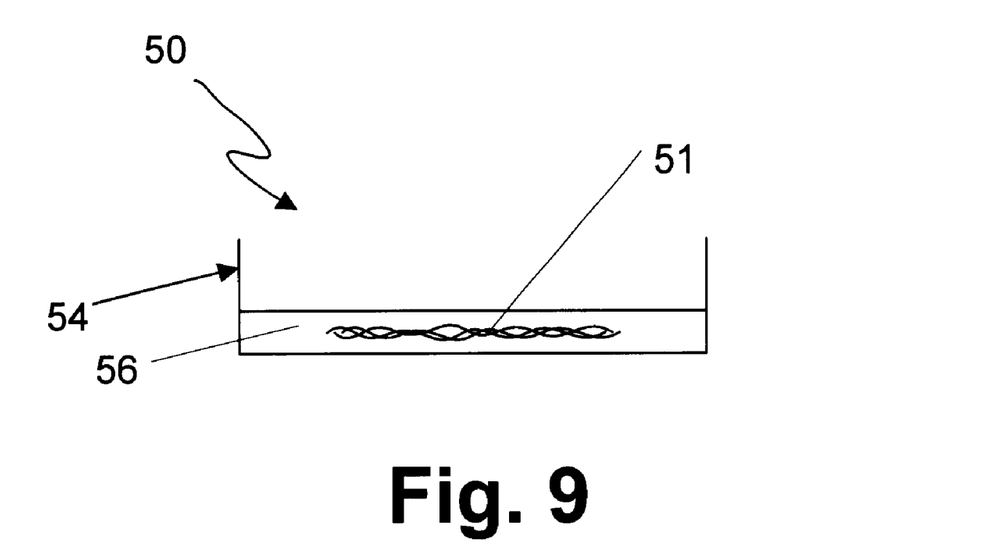
FIG. 9 is a cut-away side view of the second step used in the method of the third preferred embodiment.

In certain applications, it may be desirable to treat a portion of the sponge material with a radioisotope shortly before using the sponge. This can be accomplished by a method of radiating a medical device according to a third preferred embodiment 50. FIGS. 8–9 show the basic steps of a method according to the third preferred embodiment 50. In the third preferred embodiment 50, a portion of sponge material 51 may be provided to the medical professional as part of an activation kit. This kit contains a patch-like portion of sponge 51, a pre-measured quantity of a water soluble radioactive salt or acid, and a pre-measured quantity of an aqueous solution. The portions of the kit are measured so as to yield the desired level of radioactivity to the sponge. With knowledge of the third preferred embodiment 50 described below, one with ordinary skill in the art can determine the appropriate amounts of salt and aqueous solution.

In the preferred kit, 1 ml of radioactive Calcium Chloride ($^{45}CaCl_2$) at 10 mCi/ml, the preferred radioactive salt, is packaged in a glass vial. Furthermore, 100 ml of isotonic saline solution, the preferred aqueous solution, is also packaged in a small glass vial. The sponge 51 can vary in size depending on the application.

When ready to use the sponge 51, the medical professional simply mixes the radioactive Calcium Chloride 52 and the isotonic saline 53 in a container 54, such as a glass dish. As discussed above, radioactive Calcium Chloride 52 is water soluble and, therefore, dissociates into $^{45}Ca^{(+)}$ and $Cl^{(-)}$ ions in the isotonic saline 53, forming a solution 56. Then, the sponge 51 is placed in the container 54 and bathed with the solution 56. See FIG. 9.

As the water-soluble sponge 51 begins to break down in the solution 56, the $^{45}Ca^{(+)}$ and $Cl^{(-)}$ ions become trapped within the fibers and natural recesses of the sponge 51. Therefore, when the sponge 51 is removed from the container 54 by the medical professional for use in a patient, a portion of the $^{45}Ca^{(+)}$ ions are carried by the sponge 51 to the treatment site.

In the third preferred embodiment 50, the radioactive isotope Calcium 45 was selected as the preferred radioactive isotope. However, at least any of the other radioisotopes listed above could also easily be used with the third preferred embodiment 50. Additionally, Calcium 45 was selected to be used in the salt form of radioactive Calcium Chloride. However, Calcium 45 could also be used in non-water soluble salts, such as radioactive Calcium Fluoride ($^{45}CaF_2$), for example. Additionally, the Calcium 45 could also be used in its acid form.

With all the preferred embodiments and elements described above, it would be apparent to one skilled in the art that many variations and modifications may be made to the preferred embodiments (i.e. preferred nonlimiting examples) as described above without substantially departing from the principles of the present invention. Such variations and modifications are intended to be included herein and are within the scope of the present invention, as set forth in the following claims.

We claim:

1. A medical device for inhibiting a hyperplastic response in biological tissue, said medical device comprising:

(a) polymeric hydrocarbon molecules forming said medical device; and (b) a molecular form of a radioactive isotope entrapped within a molecular structure of said medical device by the molecular structure of said polymeric hydrocarbon molecules, wherein said radioactive isotope inhibits a hyperplastic response in biological tissue.

2. The medical device of claim 1, wherein said molecular form comprises a salt of a radioactive isotope.

3. The medical device of claim 2, wherein said radioactive isotope comprises a beta-emitting isotope.

4. The medical device of claim 3, wherein said beta-emitting isotope comprises Calcium 45.

5. The medical device of claim 2, wherein said radioactive isotope comprises a gamma-emitting isotope.

6. The medical device of claim 5, wherein said gamma-emitting isotope comprises Yttrium 90.

7. The medical device of claim 1, wherein said molecular form comprises an acid of a radioactive isotope.

8. The medical device of claim 1, wherein said medical device comprises a biodegradable material.

9. The medical device of claim 1, wherein said medical device is constructed of a biocompatable metal material and said polymeric hydrocarbon molecules are distributed over said biocompatible metal.

10. A medical device for inhibiting a hyperplastic response in biological tissue, said medical device comprising:

(a) a thrombogenic sponge; and (b) a radioactive isotope trapped within a molecular structure of said thrombogenic sponge material by the molecular structure of said thrombogenic sponge material, wherein said radioactive isotope inhibits a hyperplastic response in biological tissue.

11. The medical device of claim 10, wherein said radioactive isotope comprises a salt of a radioactive isotope.

12. The medical device of claim 10, wherein said radioactive isotope comprises a beta-emitting isotope.

13. The medical device of claim 12, wherein said beta-emitting isotope comprises Calcium 45.

14. The medical device of claim 10, wherein said radioactive isotope comprises a gamma-emitting isotope.

* * * * *